(12) United States Patent
Bluth

(10) Patent No.: US 9,433,633 B2
(45) Date of Patent: Sep. 6, 2016

(54) METHODS FOR TREATING DISEASES OF ALTERED IGE REGULATION

(75) Inventor: Martin Heath Bluth, West Hempstead, NY (US)

(73) Assignee: Martin Heath Bluth, Southfield, MI (US)

( * ) Notice: Subject to any disclaimer, the term of this patent is extended or adjusted under 35 U.S.C. 154(b) by 639 days.

(21) Appl. No.: 12/026,172

(22) Filed: Feb. 5, 2008

(65) Prior Publication Data

US 2008/0187593 A1 Aug. 7, 2008

Related U.S. Application Data

(60) Provisional application No. 60/888,384, filed on Feb. 6, 2007.

(51) Int. Cl.
| | | |
|---|---|---|
| *A61P 37/00* | (2006.01) | |
| *A61P 11/06* | (2006.01) | |
| *A61K 31/70* | (2006.01) | |
| *A61K 9/00* | (2006.01) | |

(52) U.S. Cl.
CPC .............. *A61K 31/70* (2013.01); *A61K 9/0014* (2013.01); *A61K 9/0019* (2013.01); *A61K 9/0073* (2013.01)

(58) Field of Classification Search
None
See application file for complete search history.

(56) References Cited

U.S. PATENT DOCUMENTS

| | | | | |
|---|---|---|---|---|
| 4,870,010 A | * | 9/1989 | Hayes | 424/114 |
| 5,042,472 A | * | 8/1991 | Bunin | 128/203.15 |
| 5,756,471 A | * | 5/1998 | Hillion et al. | 514/25 |
| 5,962,445 A | * | 10/1999 | Stewart | 514/182 |
| 2004/0214795 A1 | * | 10/2004 | Gross | 514/54 |

FOREIGN PATENT DOCUMENTS

WO PCTUS0853051 8/2008

OTHER PUBLICATIONS

"Total IgE in Plasma is Elevated after Traumatic Injury and is Associated with Sepsis Syndrome" by DiPiro et al., Ann. Surg. 215, 460-65 (1992).*
"Balance between Proinflammatory Cytokines and Their Inhibitors in Bronchial Lavage from Patients with Status Asthmaticus" by Tillie-Leblond et al., Am. J. Respir. Crit. Care Med. 159, 487-94 (1999).*
"Sophorolipids block lethal effects of septic shock in rats in a cecal ligation and puncture model of experimental sepsis" by Bluth et al., Crit. Care Med. 34, 188-95 (Jan. 2006).*
M.H. Bluth et al., "Sophorolipids Decrease IgE Production in U266 Cells," The Journal of Allergy and Clinical Immunology, American Academy of Asthma Allergy and Immunology, Abstract #779, Feb. 2006, p. S202.
M. Hagler et al., "Sophorolipids Decrease IgE Production in U266 Cells by Downregulation of BSAP (Pax5), TRL2, STAT3 and IL-6," The Journal of Allergy and Clinical Immunology, Abstract #1030, Jan. 2007, p. S263, vol. 119, Issue 1.

* cited by examiner

*Primary Examiner* — Theodore R West
(74) *Attorney, Agent, or Firm* — Senniger Powers LLP

(57) ABSTRACT

Techniques for treating one or more diseases of altered IgE regulation in a patient are provided. For example, a technique for treating one or more diseases of altered IgE regulation in a patient includes the step of administering a therapeutically effective amount of one or more sophorolipids to the patient in a manner which decreases IgE production in the patient. Further, the technique for treating one or more diseases of altered IgE regulation may include administering a therapeutically effective amount of one or more sophorolipids intravenously, intramuscularly, as an inhalant, subcutaneously, topically and/or systemically.

13 Claims, 7 Drawing Sheets

EXTRACELLULAR IgE

PLASMA CELL MORPHOLOGY

FIG. 5

GENE EXPRESSION PROFILES

| SOPHOROLIPID μg/ml | V | 24 HOURS | | | | | | 48 HOURS | | | | | | 72 HOURS | | | | | |
|---|---|---|---|---|---|---|---|---|---|---|---|---|---|---|---|---|---|---|---|
| | | 0.1 | 1.0 | 10 | 50 | 100 | | 0.1 | 1.0 | 10 | 50 | 100 | | 0.1 | 1.0 | 10 | 50 | 100 |
| GENE | | | | | | | | | | | | | | | | | | |
| BSAP/PAX 5 | + | − | − | − | − | − | | − | − | − | − | − | | − | − | − | − | − |
| IL6 | + | − | − | − | − | − | | + | + | + | + | + | | + | + | + | + | + |
| TLR2 | + | − | − | − | − | − | | − | − | − | − | − | | + | + | + | + | + |
| STAT3 | + | − | − | − | − | − | | + | + | + | + | + | | − | − | − | − | − |
| β-ACTIN | + | + | + | + | + | + | | + | + | + | + | + | | + | + | + | + | + |

METHODS FOR TREATING DISEASES OF ALTERED IGE REGULATION

CROSS-REFERENCE TO RELATED APPLICATION(S)

This application claims the benefit of U.S. Provisional Application Ser. No. 60/888,384, filed on Feb. 6, 2007, the disclosure of which is incorporated by reference herein.

FIELD OF THE INVENTION

The present invention relates generally to immunology and, more particularly relates to methods for treating diseases of altered IgE regulation.

BACKGROUND OF THE INVENTION

Sophorolipids are a class of microbial glycolipids and promising modulators of the immune response. Sophorolipids have been used in attempts to treat medical conditions such as sepsis. For example, existing approaches in the area of treatment of sepsis include U.S. Patent Application Publication No. US 2004/0214795 to Gross entitled "Treatment and Prophylaxis of Sepsis and Septic Shock," which includes a method and composition for the prophylaxis or treatment of humans or animals for septic shock and sepsis using a mixture of sophorolipids.

Immunoglobulin E (IgE) is an antibody subclass capable of facilitating significant immune system responses. IgE can specifically recognize certain allergens and have interactions with its known receptors which include a high affinity receptor FcεRI and low affinity receptor FcεRII, resulting in mediating inflammatory reactions. Such inflammatory reactions lead to symptoms associated with allergy and diseases such as, for example, asthma, eczema and allergic rhinitis. Individuals with diseases of altered IgE regulation (such as, for example, atopic individuals and individuals with hyper-IgE syndrome) can have as much as ten times the normal level of IgE in their blood.

As an example of an altered IgE regulation disease, asthma is a disease that affects the airways of a patient, thereby making breathing difficult. Asthma can tighten the muscles around the airways thereby restricting the air moving into and out of the lungs. Symptoms of asthma can include coughing, wheezing, shortness of breath and a tight feeling in the chest.

Existing approaches in asthma therapy, for example, effect treatment after IgE has been made and/or binds to its antigen. This approach is undesirable in that IgE that has interacted with an antigen has the capability of resulting in unwanted immune reactions, as noted above. Further, IgE that has already been made has the opportunity to interact and bind with its antigen, thereby facilitating the same undesirable immune reactions.

Accordingly, there exists a need for techniques to treat one or more diseases of altered IgE regulation which do not suffer from the above-noted problems associated with conventional treatment methodologies.

SUMMARY OF THE INVENTION

Principles of the present invention, in illustrative embodiments thereof, meet the above-noted need by providing techniques for treating diseases of altered IgE regulation in a patient.

For example, in one aspect of the invention, a technique for treating one or more diseases of altered immunoglobulin E (IgE) regulation in a patient includes the step of administering a therapeutically effective amount of one or more sophorolipids to the patient to decrease IgE production in the patient. Further, the technique for treating one or more diseases of altered IgE regulation may include administering one or more sophorolipids intravenously, intramuscularly, as an inhalant, subcutaneously, topically and/or systemically.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 5 is a diagram illustrating selected gene expression profiles at varying levels of sophorolipid administration, according to an embodiment of the present invention;

DETAILED DESCRIPTION OF THE INVENTION

Figure 1:
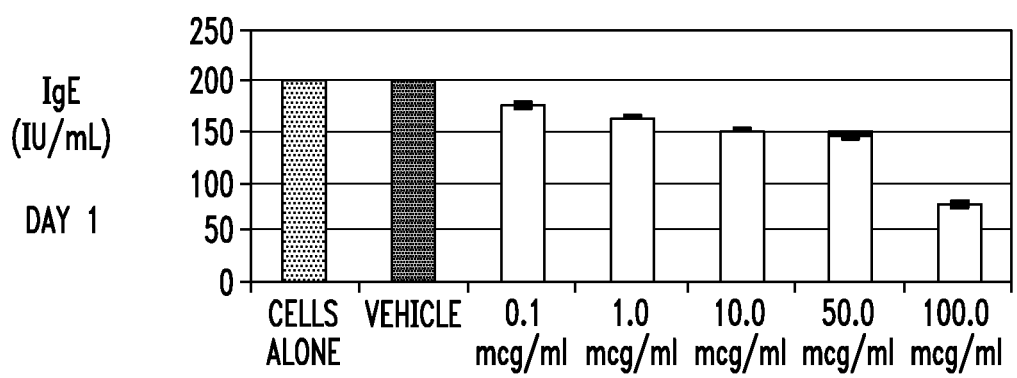
FIG. 1 is a diagram illustrating extracellular IgE amounts at varying levels of sophorolipid administration, according to an embodiment of the present invention.
Figure 1:
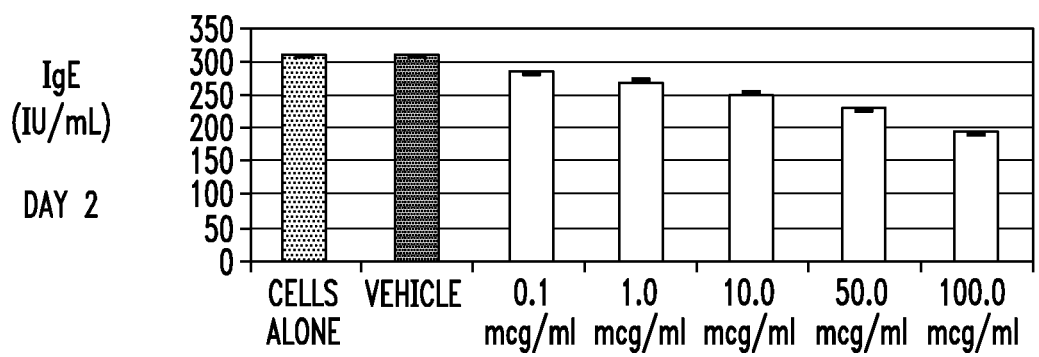
Figure 1:
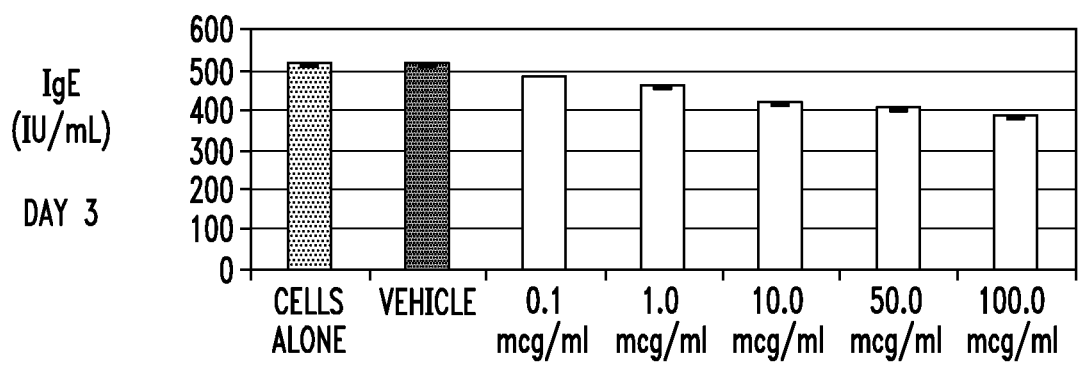

Principles of the present invention will be described in the context of an illustrative treatment methodology using sophorolipids. However, it is to be understood that the teachings presented herein are more generally applicable to methodologies for treating one or more diseases of altered IgE regulation in a patient by administering a therapeutically effective amount of one or more compounds directed to decreasing IgE production in the patient. A "therapeutically effective amount" of a given compound in a treatment methodology may be defined herein as an amount sufficient to produce a measurable decrease in IgE production in the patient. The term "patient" as used herein is intended to refer broadly to mammalian subjects, preferably humans receiving medical attention (for example, diagnosis, monitoring, etc.), care or treatment.

Sophorolipids decrease IgE production in U266 cells primarily by down-regulating important genes involved in IgE pathobiology in a synergistic manner, as well as by affecting plasma cell activity. Sophorolipids also possess anti-inflammatory activity and provide a novel therapy in diseases of altered IgE regulation.

Regulation of IgE levels can involve its receptors which include, for example, FcεRI and FcεRII (also known as CD23). CD23 regulation may facilitate an IgE-dependent mechanism of antigen presentation, whereby B cells expressing CD23 are able to present an allergen to specific T helper cells and stimulate further immune responses.

By way of example only and without loss of generality, as described herein, sophorolipids and/or their derivatives may be used in the treatment of asthma, although treatment of other diseases of altered IgE regulation are contemplated (for example, allergy). Detailed descriptions of the research and the effects of immunoglobulin treatment on asthma are provided in Bluth et al., "Sophorolipids decrease IgE production in U266 cells." *American Academy of Asthma Allergy and Immunology*, Abstract #779, published as a supplement in *Journal of Allergy and Clinical Immunology* 117, S202 (2006) and "Sophorolipids Decrease IgE Production in U266 Cells by Downregulation of BSAP (Pax5), TLR-2, STAT3 and IL-6." Hagler M, Smith-Norowitz T A, Chice S, Wallner S R, Viterbo D, Mueller C M, Gross R, Nowakowski M, Schulze R, Zenilman M E, Bluth M H, *The Journal of Allergy and Clinical Immunology* January 2007 (Vol. 119, Issue 1 (Supplement), Page S263), the disclosures of which is incorporated by reference herein. Specifically, the treatments described herein are effective in decreasing IgE production. Thus, sophorolipids and/or their derivatives, as taught in one or more embodiments of the present invention, may be administered to treat various diseases such as, for example, atopic diseases, including asthma.

Principles of the present invention include sophorolipids that may be derived from a natural mixture and/or select sophorolipid derivatives derived from *Candida bombicola* and/or any other organism capable of producing sophorolipids or derivatives.

In one illustrative example, log phase U266 (IgE producing myeloma cell line) cells were cultured in complete Roswell Park Memorial Institute medium (cPPMI)+/−increasing concentrations of sophorolipids (0.1-100 microgram per milliliter (ug/ml)) for 24-72 hours, after which levels of intracellular and extracellular IgE and immunoglobulin A (IgA) (for class switching), and soluble CD23 (sCD23) protein were determined in culture supernatants via flow cytometry and Enzyme-Linked ImmunoSorbent Assay (ELISA). Cells were assessed for proliferation via a MTT assay (an assay measuring changes in color for measuring cellular proliferation/growth), and cellular apoptosis using Annexin 5 (a probe in the annexin A5 affinity assay to detect cells which have expressed phosphatidylserine on the cell surface, a feature found in apoptosis as well as other forms of cell death) and Caspase 3 (cells that cleave other protein substrates within the cell resulting in the apoptotic process).

Cells were also assessed for changes in cell structure via the use of a confocal vehicle, cell surface expression of CD23 and CD38 (plasma cell marker), and changes in cell morphology (plasma cells/field) compared with controls (cRPMI, 20% sucrose vehicle). This data represents the number of plasma-like cells (defined as cells ≥2× the average cell diameter) per 100 cells. mRNA expression was determined for FcεRI (Fc epsilon RI, the high-affinity receptor for IgE), interleukin-6 (IL-6), interleukin-6 receptor (IL-6R), signal transducers and activator of transcription (STAT) protein 3 (STAT3), toll-like receptor 2 TLR-2, B cell-specific activator protein (BSAP) (or Paired box 5 gene (PAX5)) with β-actin as a control via reverse transcriptase dependent-polymerase chain reaction (RT-PCR).

Cell viability was determined by Trypan blue exclusion dye (>95%). This data signifies that greater than 95% of the assessed cells were viable (that is, alive). Data are reported as mean IgE international units per milliliter (IU/ml)+/−standard error (SE) and significance between groups was determined by student's t-test (statistical hypothesis test for two groups in which the test statistic has a student's t distribution if the null hypothesis is true). Also, significance among groups was determined by analysis of variance (ANOVA).

Figure 2:
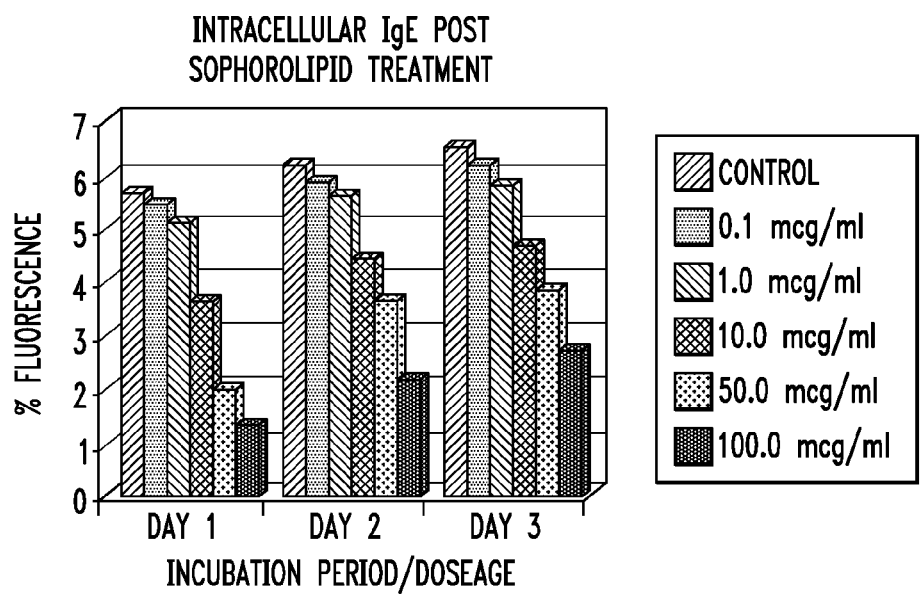
FIG. 2 is a diagram illustrating intracellular IgE amounts at varying levels of sophorolipid administration, according to an embodiment of the present invention.
Figure 3:
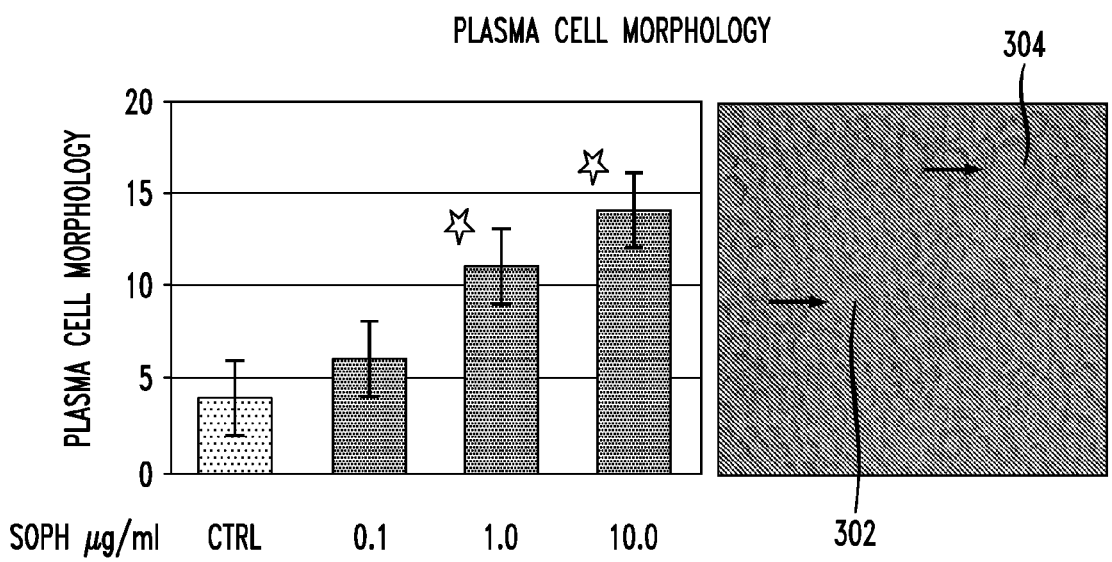
FIG. 3 is a diagram illustrating plasma cell morphology at varying levels of sophorolipid administration, according to an embodiment of the present invention.

U266 cells cultured in cRPMI or sucrose vehicle produced high levels of IgE (520 IU+/−32). As illustrated in FIGS. 2 and 3, addition of sophorolipids maximally decreased intracellular and extracellular IgE production at 24-72 hours in a dose-dependent manner ((1.0 ug/ml (416+/−8 SE), $p<0.01$; 63% reduction at 100 ug/ml, $p<0.001$)). Similar numbers of sCD23 and cell surface expression of CD23 and CD38 were detected in treatment versus control groups (sCD23: below detection limits (not shown). Cell surface expression of CD23 was detected at levels of 14%+/−3%, while CD38 was detected at greater than 95%.

Figure 7:
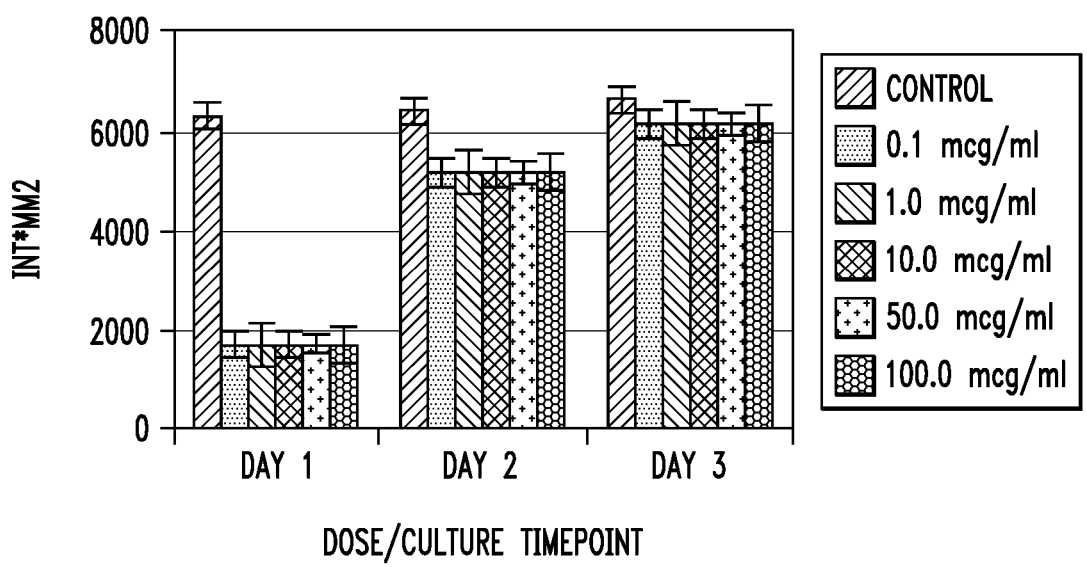
FIG. 7 is a diagram illustrating IL-6 mRNA expression at varying levels of sophorolipid administration, according to an embodiment of the present invention.
Figure 8:
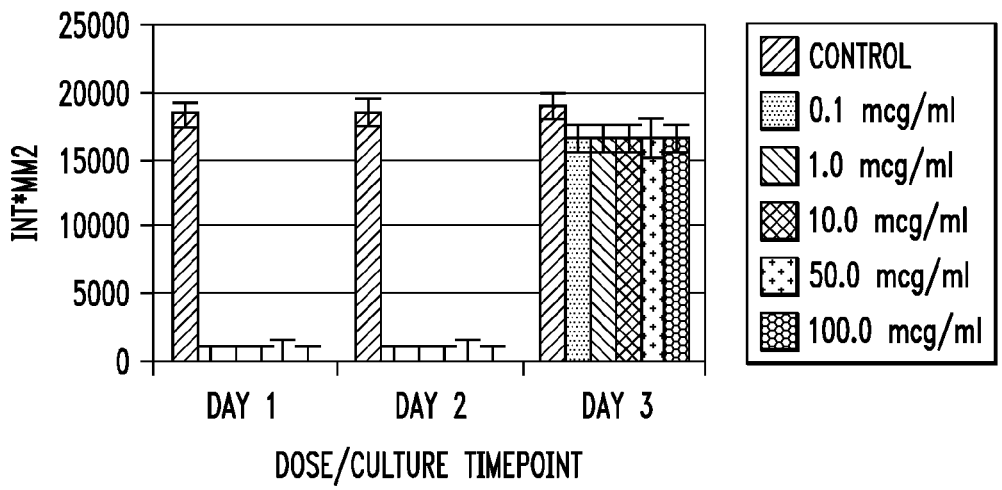
FIG. 8 is a diagram illustrating TLR-2 mRNA expression at varying levels of sophorolipid administration, according to an embodiment of the present invention.
Figure 9:
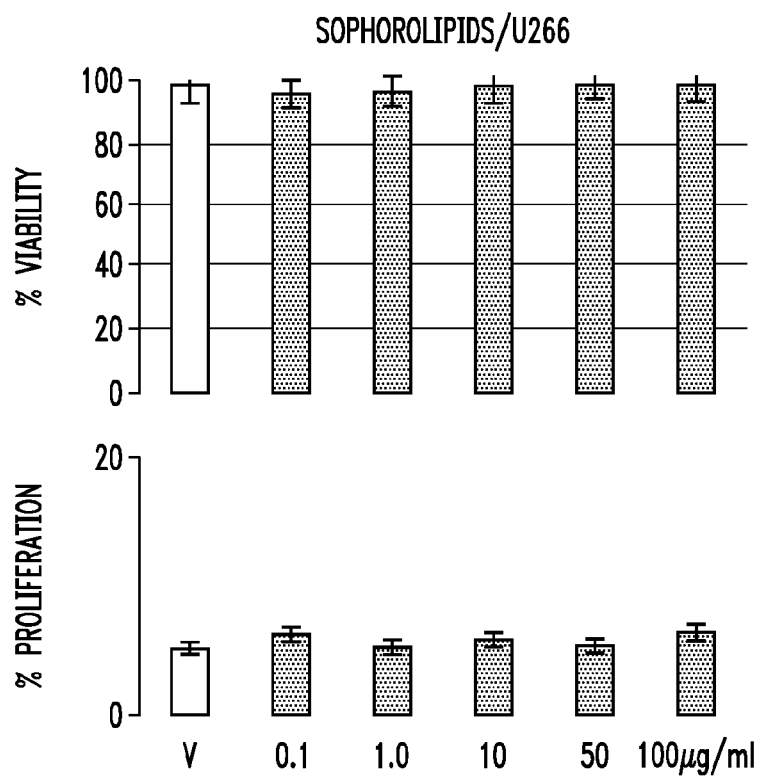
FIG. 9 is a diagram illustrating viability and proliferation percentages of U266 cells at varying levels of sophorolipid administration, according to an embodiment of the present invention.

Addition of increasing sophorolipid concentration (10 ug/ml) correlated with a bimodal cell surface expression of CD38 and an increase in the percentages of plasma-like cells compared with controls (14%, 4% respectively; $p<0.05$). As illustrated in FIGS. 7-9, sophorolipid treatment decreased mRNA expression of BSAP (Pax5) at 24-72 hours, TLR-2 at 24-48 hours, and STAT3 and IL-6 at 24 hours when compared with untreated/vehicle controls. Also, β-actin was not affected. As illustrated in FIG. 9, sophorolipid treatment did not affect cellular structure or proliferation. Furthermore, sophorolipid treatment did not affect apoptosis, IgA production, FcεI, or IL-6R mRNA expression when compared with controls.

No adverse effects have been reported in laboratory animals at doses described herein. Also, sophorolipids and/or their derivatives, as used herein, can be easily chemically modified to augment target cells of interest and potency.

Given the above realizations made in accordance with one or more embodiments of the present invention, and general features associated therewith, the remainder of the detailed description will provide an illustrative explanation of techniques for implementing such realizations and features in the context of FIGS. 1 through 10.

FIG. 1 is a diagram illustrating extracellular IgE amounts at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and production of IgE, in IU per milliliter, was determined after 24, 48 and 72 hours. These data demonstrate a decrease in the expression of IgE production which is proportional with sophorolipid treatment when compared with no treatment (vehicle only control).

FIG. 2 is a diagram illustrating intracellular IgE amounts at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and production of intracellular IgE, determined as percent fluorescence, was determined after 24, 48 and 72 hours. These data demonstrate a decrease in the expression of intracellular IgE production which is proportional with sophorolipid treatment when compared with no treatment (vehicle only control).

FIG. 3 is a diagram illustrating plasma cell morphology at varying levels of sophorolipid administration, according to an embodiment of the present invention. Sophorolipids were administered to cultures of U266 cells (IgE producing myeloma cell line) at concentrations ranging from 0.1-10.0 micrograms per milliliter and percentage of plasma like cells, represented as plasma cell morphology (left picture), which is defined as cells (for example, 302, 304) greater than twice (2×) the mean cellular diameter (arrows right picture), was determined after 24 hours. These data demonstrate an increase in the expression of plasma like cell which increases with sophorolipid treatment when compared with no treatment (vehicle only control).

Figure 4:
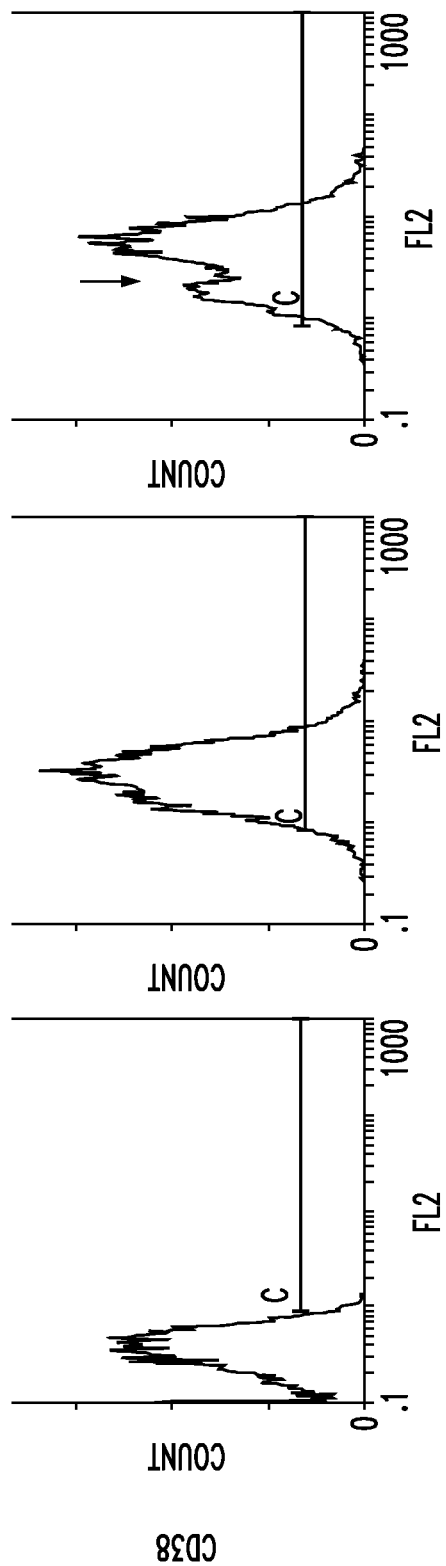
FIG. 4 is a diagram illustrating plasma cell morphology via CD38 cell count at varying levels of sophorolipid administration, according to an embodiment of the present invention.

With reference now to FIG. 4, a diagram is depicted illustrating plasma cell morphology via CD38 cell count at varying levels of sophorolipid administration, according to an embodiment of the present invention. Sophorolipids were administered to cultures of U266 cells (IgE producing myeloma cell line) at concentrations ranging from 0.1-10.0 micrograms per milliliter and distributions of cell surface expression of CD38 (plasma cell marker) was determined by flow cytometry after 24 hours. The left figure represents background fluorescence of un-labeled cells, the middle figure represents untreated cells labeled with fluorescence conjugated anti-CD38 antibody, and the right figure represents sophorolipid treated cells labeled with fluorescence conjugated anti-CD38 antibody demonstrating a bimodal distribution of cell populations. Because the differences in peak expression can be related to either cell size and that cell size has been reported to correlate with cell activity (for example, IgE antibody production), these differences in CD38 fluorescence patterns further support the findings that sophorolipids directly affect IgE production.

FIG. 5 is a diagram illustrating selected gene expression profiles at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and expression of genes involved in immunoglobulin production (BSAP/Pax5, interleukin 6 (IL-6), toll-like receptor 2 (TLR-2), STAT-3) were determined by polymerase chain reaction (PCR) after 24, 48 and 72 hours. As shown in figure, expression of all genes was decreased at varying time points with sophorolipid treatment when compared with no treatment (vehicle only control). Furthermore, structural gene (β-actin) was not affected. Additionally, as used herein, "+" indicates that the element in question was present or observed, and "−" indicates that the element in question was absent or not detected.

Figure 6:
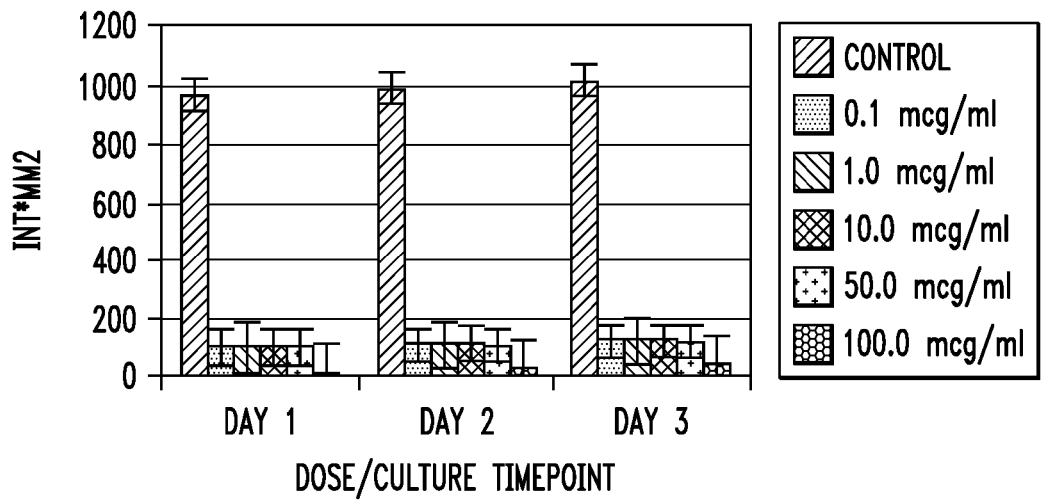
FIG. 6 is a diagram illustrating BASP/Pax5 MRNA expression at varying levels of sophorolipid administration, according to an embodiment of the present invention.

With reference now to FIG. 6, a diagram is depicted illustrating BASP/Pax5 mRNA expression at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and BSAP/Pax5 gene expression was determined by PCR after 24, 48 and 72 hours and quantified by densitometry. As shown in FIG. 6, gene expression of BSAP/Pax5 was decreased at all concentrations and at all time points when compared with no treatment (vehicle only control). Because BSAP/Pax5 is important in immunoglobulin class switching to the IgE isotype, the observation that sophorolipids decreased expression of this gene provides a mechanism for sophorolipid-dependent downregulation of IgE and its application to asthma and other diseases of altered IgE regulation.

FIG. 7 is a diagram illustrating IL-6 MRNA expression at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and IL-6 gene expression was determined by PCR after 24, 48 and 72 hours and quantified by densitometry. As apparent from FIG. 7, gene expression of IL-6 was decreased at all concentrations at 24 hours when compared with no treatment (vehicle only control). Because IL-6 is a known pro-inflammatory mediator in asthma and other diseases, and is also involved in IgE regulation, the observation that sophorolipids decreased expression of this gene provides a mechanism for sophorolipid-dependent downregulation of IgE and its application to inflammatory diseases such as, for example, asthma and other diseases of altered IgE regulation.

FIG. 8 is a diagram illustrating TLR-2 mRNA expression at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and TLR-2 gene expression was determined by PCR after 24, 48 and 72 hours and quantified by densitometry. As shown in figure, gene expression of TLR-2 was decreased at all concentrations at 24 and 48 hours when compared with no treatment (vehicle only control). Because TLR-2 is correlated with asthma, the observation that sophorolipids decreased expression of this gene provides a mechanism for sophorolipid-dependent downregulation of IgE and its application to inflammatory diseases such as, for example, asthma and other diseases of altered IgE regulation.

FIG. 9 is a diagram illustrating viability and proliferation percentages of U266 cells at varying levels of sophorolipid administration, according to an embodiment of the present invention. Sophorolipids were administered to cultures of U266 cells (IgE producing myeloma cell line) at concentrations ranging from 0.1-100.0 micrograms per milliliter and percent cellular viability (top figure) and ability of the cell to proliferate (bottom figure) was determined after 24-72 hours. As apparent from FIG. 9, sophorolipid treatment did not affect either of these parameters when compared with no treatment (vehicle only control).

One or more embodiments of the present invention illustrate an effect of sophorolipids in vivo (for example, in an in vivo asthma model). As described herein, a well established mouse ovalbumin model was employed and the ability of sophorolipids to decrease IgE, activation of ovalbumin (OVA) specific IgE in blood and bronchoalveolar lavage (BAL) fluid and pulmonary leukocytic infiltration was assessed. Sophorolipids were administered via nebulization, as this is a common route of therapeutic administration (that is, albuterol) during an acute asthmatic episode.

Figure 10A:
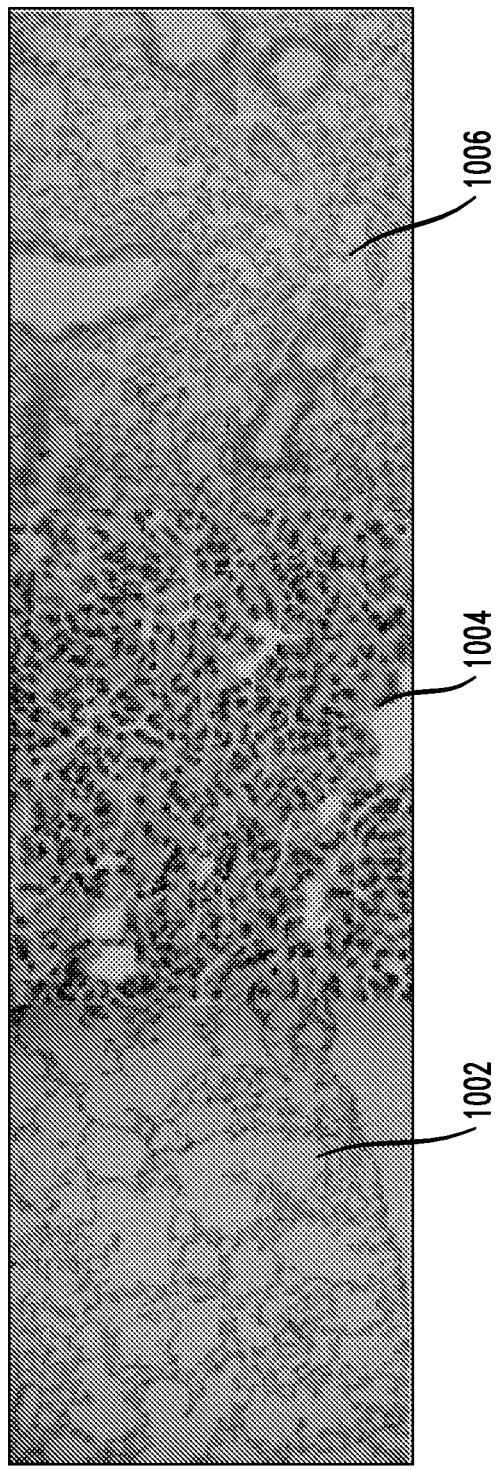
FIG. 10A is a diagram illustrating the effect of sophorolipids on asthma severity in vivo, according to an embodiment of the present invention.

Also, asthmatic mice were treated pre- and post-full OVA asthmatic insult to determine if sophorolipid treatment can be given prophylactically. As shown in FIG. 10, mice exposed to a full OVA induction regimen demonstrated pulmonary evidence of asthma. Lungs obtained from these animals showed excessive leukocytic infiltration and edema (FIG. 10A). In contrast, asthmatic animals given nebulized sophorolipids had decreased leukocytic infiltrate and edema.

Figure 10B:
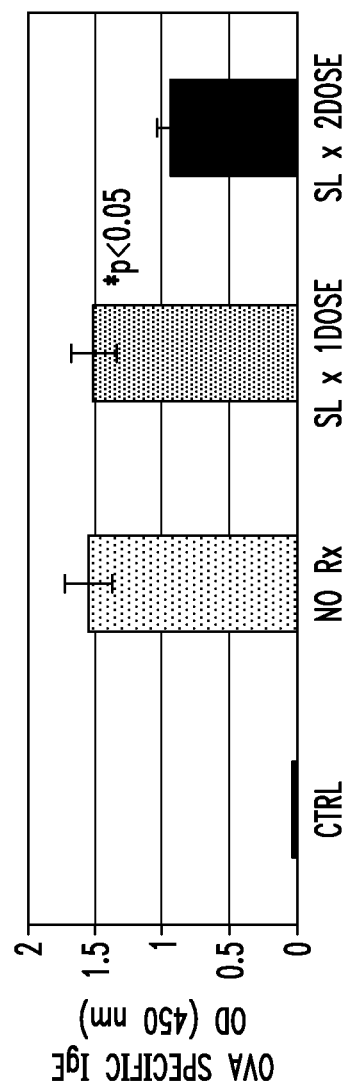
FIG. 10B is a diagram illustrating the effect of sophorolipids on asthma severity in vivo, according to an embodiment of the present invention.

Furthermore, sophorolipid treated animals had decreased levels of BAL fluid OVA specific IgE after two treatments when compared with non-treated asthmatic mice (FIG. 10B). Blood/serum levels of IgE and OVA specific IgE and BAL total IgE levels did not differ between treated versus control animals. Accordingly, such data provides strong support for the ability of sophorolipids to decrease asthma severity in vivo and serve as a novel therapy in allergic asthma.

FIG. 10A and FIG. 10B are diagrams illustrating the effect of sophorolipids on asthma severity in vivo. Mice (c57/Black6) were induced with experimental asthma by the ovalbumin/alum model. Animals were treated at indicated time points with either sophorolipids in vehicle (20% sucrose) or vehicle alone, and animals were sacrificed at day 14 of the experimental protocol.

As illustrated in FIG. 10A, lungs were analyzed for evidence of asthma severity, as defined by increased leukocytic infiltrate and edema. The data depicted in FIG. 10A represent sections from normal: mice 1002 (left panel), OVA-sensitized asthmatic mice 1004 (middle panel), and sophorolipid treated asthmatic mice 1006 (right panel). As depicted in FIG. 10A, N=5 mice per group with similar results. Furthermore, data were similar whether sophorolipids were administered pre- or post-OVA asthma induction. The demonstration that sophorolipid administration decreased asthma severity in an animal model of experimental asthma postulates its use as a therapeutic intervention.

Also, as illustrated in FIG. 10B, BAL fluid obtained from asthmatic and sophorolipid treated animals were assessed for OVA specific IgE antibodies after one or two doses compared with no treatment (no Rx). As depicted in FIG. 10B, control equals normal mouse BAL fluid, and data represent mean ±standard deviation (SD). Significance was determined by student's t-test, $p<0.05$ (two treatments compared with one or no treatment groups, and n=5 mice per group). As such, decreased OVA-specific IgE antibodies correspond with the observed decrease in asthma severity with sophorolipid treatment in the OVA animal asthma model.

As described above, sophorolipids have beneficiary effects in several cases of immuno-derived pathologies, such as asthma and sepsis, which in many respects have similarities in their underlying inflammatory activity. Furthermore, it is demonstrated herein that SL were able to decrease in vitro and in vivo IgE production in cell and animal models of asthma. Sophorolipids can, for example, decrease intra and extracellular IgE production in vitro, in an IgE producing cell line.

This IgE downregulatory effect can be due, for example, to sophorolipid mediated reduction in the expression of genes involved in IgE regulation including BSAP/Pax 5, IL-6, TLR2 and STAT3. These genes, both independently or synergistically, may be responsible in part for the decreased production of IgE in vitro and may also provide a mechanism of action for sophorolipids' anti-IgE effects. Furthermore, sophorolipids decrease asthmatic severity in an in vivo model of experimental asthma, in that administration of sophorolipids decreased leukocytic infiltration, edema and antigen specific IgE levels.

Sophorolipids are unique in that they can be chemoenzymatically modified to produce unique purified derivatives which have differential anti-inflammatory effects. Also, that these agents did not alter cellular or animal viability or proliferative capacity in these inflammatory models makes them attractive agents. As detailed herein, sophorolipids decrease IgE production and have the ability to reduce asthma severity (for example, in a mouse asthma model). In addition to possessing anti-inflammatory effects and being able to increase survival in experimental animal sepsis, sophorolipids are able to decrease IgE production in a B cell model by downregulating genes involved in IgE regulation in a dose dependent manner. Furthermore, sophorolipids are able to decrease asthma severity when administered before and after asthma induction, suggesting its potential therapeutic utility both prophylacticaly and as a treatment for acute exacerbations.

In a preferred embodiment of the present invention, one or more diseases of altered IgE regulation are treated in a patient by administering a therapeutically effective amount of one or more sophorolipids to the patient to decrease IgE production in the patient. As illustrated in the above figures, decrease in IgE production may include and/or be a result of, for example, anti-inflammatory activity.

Administration of sophorolipids and/or their derivatives may include dissolving the sophorolipids and/or derivatives in a pharmaceutically acceptable carrier. Suitable carriers may include, for example, ethanol, saline, dimethyl sulfoxide (DMSO), sucrose, or any other commonly used carrier.

Administration of sophorolipids and/or their derivatives may include administering amounts in an amount in the range of 0.5 milligrams per kilogram of body weight of a patient to 750 milligrams per kilogram of body weight of a patient. Also, sophorolipids and/or their derivatives may be administered one or more times daily for a period of one or more days.

For treatments being administered intravenously or intramuscularly, the solutions must be prepared in a suitable, injectable and sterile, form. Suitable injectable forms may include, but are not limited to, aqueous solutions and dispersions prepared in pharmaceutically acceptable carriers such as, for example, water, ethanol, glycerol, propylene glycol, liquid polyethylene glycol, vegetable oils, and the like. Further, the solutions should be prepared and stored in a sterile form and be adequately protected against contamination by microorganisms such as, for example, fungi, bacteria and viruses. Contamination may be prevented by the use of antimicrobial agents such as, for example, parabens, chlorobutanol, phenol, sorbic acid, thimerosal, and the like.

In another illustrative embodiment of the present invention, sophorolipids and/or their derivatives are administered to the patient as an inhalant. The inhalant may be in the form of an aerosol. Sophorolipids and/or their derivatives administered as an inhalant allow for the direct treatment of areas of the respiratory tract. Thus, administering sophorolipids and or/their derivatives in the form of an inhalant is useful for, but not limited to, the treatment of respiratory disorders or diseases such as, for example, asthma and asthma-related conditions.

In the one or more embodiments wherein sophorolipids and/or their derivatives are administered as an inhalant, the sophorolipids and or/their derivatives should be contained in, or formed into, particles of a size sufficiently small to pass through the mouth and larynx upon inhalation and into the bronchi and alveoli of the lungs. The particles can have a size in the range of, for example, about one to about ten microns in diameter.

In another illustrative embodiment, sophorolipids and/or their derivatives are administered to a patient topically. Topical applications are particularly useful for direct localized treatment, as well as particularly useful for treating diseases of altered IgE regulation such as, for example, skin allergies, eczema and the like. Topical applications may include the application of topical treatments including, but not limited to, ointments, creams, salves, transdermal patches, as well as any combination of the foregoing topical treatments. Ointments or creams may be prepared comprising sophorolipids and/or their derivatives and a suitable ointment or cream delivery medium. The ointment or cream may be applied to the areas of the patient requiring the treatment. The sophorolipids and/or their derivatives contained in the ointment or cream will diffuse transdermally into the body of the patient providing treatment to the effected area.

Additionally, as mentioned above, sophorolipids and/or their derivatives may be administered using a transdermal patch. A transdermal patch may be worn on the skin of the patient like, for example, a bandage. A transdermal patch allows for a prolonged treatment to be administered. For example, a patient may wear a transdermal patch for a plurality of hours and receive low dose treatments throughout that period. Other applicable treatment methods may be used in accordance with the teachings of the present invention. For example, a solution comprising sophorolipids and/or their derivatives may be injected or otherwise administered subcutaneously.

Sophorolipids and/or their derivatives may also be administered, for example, systemically as well as at a site of inflammation and/or rejection.

Because principles of the present invention illustrate that sophorolipids decrease and/or modulate expression of important genes involved in general immunoglobulin production, the foregoing techniques are provided merely as exemplary methodologies for administering treatment to a patient, and it is to be appreciated that the teachings of the present invention are generally applicable to any suitable methodology and should not be limited to any particular techniques described herein.

The foregoing techniques may be used to treat any disorder wherein the pathology lies in the diseases of altered immunoglobulin production. Further, in an illustrative embodiment, sophorolipids and/or their derivatives are used in the treatment of an autoimmune disease. The teachings of the present invention are applicable to the treatment of autoimmune diseases including, but not limited to, the following disease states: Guillain-Barre syndrome, Kawasaki syndrome, dermatomyositis, immune thrombocytopenic purpura (ITP), chronic inflammatory demylinating polyneuropathy, multifocal motor neuropathy, autoimmune hemolytic anemia, myasthenia gravis, Lambert-Eaton syndrome, Churg-Strauss vasculitides, multiple sclerosis, bullous pemphigoid, heparin-induced thrombocytopenia (HIT), post transfusion purpura (PTP), as well as any combination of the foregoing disease states.

In another illustrative embodiment, the sophorolipids and/or their derivatives are administered for the treatment of atopy and atopic diseases. Atopy is the predisposition for developing an IgE-mediated response to common environmental allergens. For example, atopic diseases include diseases such as hay fever, atopic dermatitis (eczema) and Job's syndrome. Also, atopy is the strongest identifiable predisposing factor for developing asthma.

In another illustrative embodiment, the sophorolipids and/or their derivatives are administered for the treatment of allergic diseases as well as inflammatory diseases.

While the present invention has been described in accordance with the treatment of diseases and disorders described herein, it is to be appreciated that the teachings of the present invention are generally applicable to any diseases or disorders necessitating immunoglobulin treatment. Thus, the teachings of the present invention should not be construed as being limited to the treatment of any particular disease or disorder.

Although illustrative embodiments of the present invention have been described herein with reference to the accompanying drawings, it is to be understood that the invention is not limited to those precise embodiments, and that various other changes and modifications may be made therein by one skilled in the art without departing from the scope of the appended claims.

What is claimed is:

1. A method of treating asthma comprising administering one or more sophorolipids to a patient in need thereof in an amount which is effective to decrease IgE production wherein the one or more sophorolipids are administered one or more times daily for a period of one or more days and in an amount in the range of 0.5 milligrams per kilogram of body weight of the patient to 750 milligrams per kilogram of body weight of the patient.

2. The method of claim 1, wherein the step of administering one or more sophorolipids comprises dissolving the one or more sophorolipids in one or more pharmaceutically acceptable carriers.

3. The method of claim 2, wherein the one or more carriers comprise at least one of saline, dimethyl sulfoxide (DMSO), sucrose or ethanol.

4. The method of claim 1, wherein the one or more sophorolipids is administered intravenously.

5. The method of claim 1, wherein the one or more sophorolipids is administered intramuscularly.

6. The method of claim 1, wherein the one or more sophorolipids is administered as an inhalant.

7. The method of claim 6, wherein the inhalant comprises an aerosol.

8. The method of claim 6, wherein the one or more sophorolipids are in the form of one or more particles, and wherein each particle has a size of about one micron in diameter to about ten microns in diameter.

9. The method of claim 1, wherein the one or more sophorolipids are administered subcutaneously.

10. The method of claim 1, wherein the one or more sophorolipids are administered topically.

11. The method of claim 10, wherein the one or more sophorolipids are topically administered as a cream, salve, transdermal patch or ointment.

12. The method of claim 1, wherein the one or more sophorolipids are administered systemically.

13. The method of claim 1, wherein the one or more sophorolipids are administered at a site of inflammation or rejection.

* * * * *